(12) United States Patent
Ball

(10) Patent No.: US 11,653,952 B2
(45) Date of Patent: May 23, 2023

(54) METHOD AND APPARATUS FOR IMPROVING BONE SCREW IMPLANTS

(71) Applicant: Bret G. Ball, Lake Oswego, OR (US)

(72) Inventor: Bret G. Ball, Lake Oswego, OR (US)

(\*) Notice: Subject to any disclaimer, the term of this patent is extended or adjusted under 35 U.S.C. 154(b) by 137 days.

(21) Appl. No.: 16/948,373

(22) Filed: Sep. 15, 2020

(65) Prior Publication Data

US 2022/0079630 A1 Mar. 17, 2022

(51) Int. Cl.
*A61B 17/70* (2006.01)
*A61B 17/68* (2006.01)

(52) U.S. Cl.
CPC ...... *A61B 17/7032* (2013.01); *A61B 17/7082* (2013.01)

(58) Field of Classification Search
CPC ........ A61B 2017/8655; A61B 17/8685; A61B 17/84; A61B 17/86; A61B 17/8625–8635; A61B 17/7032–704; A61B 17/7082; F16B 13/124

See application file for complete search history.

(56) References Cited

U.S. PATENT DOCUMENTS

| | | | |
|---|---|---|---|
| 5,236,445 A * | 8/1993 | Hayhurst | A61B 17/0401 606/232 |
| 8,388,660 B1 | 3/2013 | Abdou | |
| 9,247,975 B2 * | 2/2016 | Erhart | A61B 17/863 |
| 9,421,040 B2 * | 8/2016 | Beger | A61B 17/8605 |
| 10,507,041 B2 * | 12/2019 | Tsai | A61F 2/0811 |
| 2004/0210313 A1 * | 10/2004 | Michelson | A61F 2/446 623/17.11 |
| 2005/0055024 A1 * | 3/2005 | James | A61B 17/1668 606/64 |
| 2008/0027444 A1 * | 1/2008 | Malek | A61B 17/686 606/86 A |
| 2008/0221623 A1 * | 9/2008 | Gooch | A61B 17/686 606/302 |
| 2011/0106177 A1 * | 5/2011 | Lewis | A61B 17/686 606/305 |
| 2011/0112576 A1 * | 5/2011 | Nguyen | A61B 17/0401 606/232 |
| 2014/0277193 A1 * | 9/2014 | Mobasser | A61B 17/8625 606/311 |
| 2017/0100177 A1 * | 4/2017 | Kim | A61B 17/864 |

(Continued)

FOREIGN PATENT DOCUMENTS

WO WO-2012121726 A1 * 9/2012 ........... A61B 17/863

OTHER PUBLICATIONS

"Buttress thread"—Wikipedia.org, Nov. 11, 2016 <https://web.archive.org/web/20161111043717/https://en.wikipedia.org/wiki/Buttress_thread> (Year: 2016).*

(Continued)

*Primary Examiner* — Julianna N Harvey
*Assistant Examiner* — Anna V. Little
(74) *Attorney, Agent, or Firm* — Howard Russell

(57) ABSTRACT

Bone attachment shim device composed of a biomaterial compatible with bone and provides an enhanced surface area on the outer surface of the device for engaging the bone, an enhanced surface area within the device for engaging the bone screw, and is composed of a partial shaft design which is greater than 180 but less than 270 degrees around when viewed in cross section. The device preferably has a biased tip for facilitating placement into bone tissue.

18 Claims, 12 Drawing Sheets

(56) References Cited

U.S. PATENT DOCUMENTS

2017/0296344 A1* 10/2017 Souza ............... A61B 17/7055
2018/0070986 A1*  3/2018 Agarwal ........... A61B 17/7061

OTHER PUBLICATIONS

Eur Spine J, Evaluation of a transpedicular drill guide for pedicle screw placement in the thoracic spine, May 29, 2003, 11 pages, posted at ncbi.nlm.nih.gov, [online], [site visited Sep. 29, 2020], available from Internet, <URL: https://www.ncbi.nlm.nih.gov/pmc/articles/PMC3468009/>.

Med Sci Monit, Thoracic Pedicle Screw Placement Guide Plate Produced by Three-Dimensional (3-D) Laser Printing, May 19, 2016, 12 pages, posted at ncbi.nlm.nih.gov, [online], [site visited Sep. 29, 2020], available from Internet, <URL: https://www.ncbi.nlm.nih.gov/pmc/articles/PMC4917319/>.

Yu, C., Ou, Y., Xie, C. et al., Pedicle screw placement in spinal neurosurgery using a 3D-printed drill guide template: a systematic review and meta-analysis, Jan. 3, 2020, 31 pages, posted at josr-online.biomedcentral.com, ©2020 BioMed Central Ltd, [online], [site visited Sep. 29, 2020], available from Internet, <URL: https://josr-online.biomedcentral.com/articles/10.1186/s13018-019-1510-5>.

Invibio, Interbody Fusion Devices Made With Peek-Optima™ Polymers, 5 pages, posted at invibio.com, ©2020 Copyright Invibio Ltd., [online], [site visited Sep. 29, 2020], available from Internet, <URL: https://invibio.com/spine/spinal-interbody-fusion>.

J Korean Neurosurg Soc, A Case of Pedicle Screw Loosening Treated by Modified Transpedicular Screw Augmentation with Polymethylmethacrylate, Jan. 31, 2011, 6 pages, posted at ncbi.nlm.nih.gov, [online], [site visited Sep. 29, 2020], available from Internet, <URL: https://www.ncbi.nlm.nih.gov/pmc/articles/PMC3070902/>.

* cited by examiner

METHOD AND APPARATUS FOR IMPROVING BONE SCREW IMPLANTS

CONTINUITY AND CLAIM OF PRIORITY

This is an original U.S. patent application.

FIELD

The invention relates to an apparatus and methods for improving patient outcomes in the placement of bone screws, and more particularly to a shim apparatus, and associated methods of use, for facilitating proper placement of spinal and pedicle screws within vertebral columns and other bone structures.

BACKGROUND

Bone screws are used in a variety of surgeries which require implants into the skeletal system of a patient. Bone screws are commonly used to attach implants such as hip replacements, or to attach plates to bone following a traumatic injury. Screw failure resulting from a mispositioned screw can include vascular and neurological deficits (radicular pain, and motor and sensory dysfunction), dural tear, pain, pseudarthrosis, radiculopathy, and pedicle fracture due to instruments loosening, bending, and pulling out. Additionally, even with a properly positioned bone screw, there is still a risk of screw failure and bone injury due to the screw loosening, screws shifting within the patient, and screws pulling out of the bone (bending). Complications associated with bone screws negatively impact patient outcomes and generally require additional surgeries to repair.

Pedicles are short projections of bone that come directly off the back of vertebral bodies. Each pedicle lies between the back of each vertebral body and what is known as a transverse process. There are two pedicles per vertebra, one on each side of the spinal cord. Outer cortical, or compact, bone material of each pedicle defines a channel of softer cancellous bone through which a spinal stabilization screw may advantageously pass through and into a cortical and cancellous bone portions of the vertebral body. Since each pedicle is essentially elliptical in cross-section shape, wherein the cortical bone forming a circumference of the ellipse encloses softer cancellous bone of the pedicle, it will be appreciated that there are upper and lower larger area portions of the channel of the pedicle comprising cancellous bone material which does not provide a sufficiently rigid upper and lower structure for strong engagement of a pedicle screw. Therefore, it is common for pedicle screw placements to be come loose over time as forces associated with bending, twisting, and stretching movement of a person having received a spinal stabilization surgery. Accordingly, means for improving the engagement of a pedicle screw with the cortical bone sides of the channel of the pedicle, which sides are closer to the screw than upper or lower portions of cortical bone of the pedicle, would be advantageous.

Bone screws, and in particular vertebral pedicle screws, are also commonly used in vertebral fusion surgeries to treat back pain. Back pain is among the most common medical problems experienced by individuals as they age and has a variety of different causes including degenerative disc disease, trauma, ruptured or bulging discs, arthritis, and sciatica, among other causes. In many cases, including in cases of degenerative disc disease, one of the most common causes of back pain, spinal fusion surgery is required to alter the distribution of weight along the spine, as to relieve pressure in discs and reduce a patient's back pain. Such surgeries generally require the use of bone screws in order to facilitate the alteration of the bone structure as required for a positive patient outcome. In the United States alone it is estimated that surgeons perform over 1.62 million instrumented spinal fusions surgeries per year, with complications reportedly resulting from pedicle screws occurring in approximately 2.5% of cases. Further, it is estimated that there may up to a 24% error in placement of pedicle screws, which often results in multiple receiving channels, or tracts, having to be created, as with a piercing tool, into a patient's spine, or improperly placed screws having to be removed and replaced in the proper location. Accordingly, pedicle screw complications impact thousands of patients each year.

Bone screws used in spinal surgery are referred to as vertebral pedicle screws, and they have been used in spinal surgeries for decades. Vertebral pedicle screws are implanted into the vertebral pedicle, a dense stem-like structure which projects adjacent the posterior of the spine. Vertebral pedicle screws are often used in spinal surgery to correct deformity, treat trauma, to affix rods or plates to the spine, and to assist in holding bony structures together in spinal fusion surgeries. Vertebral pedicle screws are most often used in the lumbosacral spine, but can also be implanted into the thoracic, sacral, and cervical vertebra where necessary. Vertebral pedicle screws serve to anchor bone tissue together by engaging the hard-cortical bone surface along the pedicle and in the vertebral body to the surface of the screw, primarily along the threads which engage the bone surface.

Vertebral pedicle screws are usually implanted in the spine of a patient with use of imaging techniques, such as x-ray or fluoroscopy, to determine the proper depth and angle for screw placement. Once the proper screw placement has been ascertained, a receiving channel, or tract, has been created, as with a piercing tool, from the surface of the skin and into the vertebral pedicle, whereupon the screw has been inserted. However, even with the use of proper imaging techniques, improper forming of the receiving channel and screw mispositioning have remained significant risks of spinal surgery, and they have often resulted in serious complications to the patient. Not only have complications resulted from a mispositioned screw, again having included vascular and neurological deficits (radicular pain, motor and sensory dysfunction), dural tear, pain, pseudarthrosis, radiculopathy, and pedicle fracture, and screw bending due to instruments loosening and pulling out, but even properly positioned pedicle screws have failed over time. Such risk of failure of properly positioned screws have included the possibility of screw failure and pedicle injury due to screws having loosened, screws having shifted within the patient, screws having pulled out of the pedicle (bending), which have occurred with the passage of time due to inadequate bone to screw interface, and these conditions have resulted in similar complications and poor patient outcomes.

Current bone screws presently used to affix bone implants, including pedicle screws used in spinal fusion surgeries, generally have not provided an adequate surface area interaction between the cortical bone surface of the spine and the pedicle screw, which is why screw failure has occurred, and such has been increasingly likely to occur the longer a pedicle screw has remained in place. Complications associated with pedicle screws have been especially noteworthy in patients that have required long vertebral fusions (e.g. 6-7 vertebral fusions). In such cases, the pedicle screws at the top of the vertebral fusion case have been placed under abnormally high stress and have been highly prone to screw failure, wherein prior art pedicle screws have failed to provide a permanent solution for patients experiencing back pain who have required long vertebral fusions.

Further, current pedicle screws used in spinal fusion surgeries generally have not provided for a reliable method of insertion into a receiving channel where an improper receiving channel has occurred. In such cases, it has been difficult to align the pedicle screw into a properly formed receiving channel (after an improperly created receiving channel has occurred), and the pedicle screw has therefore lacked support along a correctly-formed surface of the correctly-formed channel closely adjacent the improperly positioned channel. This has increased the risk of screw insert failure due to reduction of cortical bone surface area, and it has also raised the risk of complications with the surgery because it has been difficult to place a screw in the proper channel when an improper channel has been formed, as with a piercing tool.

As such, there remains a need in the art for an attachment device which will promote the attachment of vertebral pedicle screws to the cortical surface of the bone in order to reduce the risk of complications, and to improve patient outcomes. Similarly, there also remains a need in the art for an attachment device which will allow surgeons to properly position vertebral pedicle screws in a patient, even after an improper receiving channel has been formed. In addition, attachment devices that help to facilitate the accurate placement of pedicle screws will also reduce the difficulty of spinal fusion surgeries and improve patient outcomes.

SUMMARY

The present invention addresses various problems of current pedicle screw and spinal fixation systems. In response to the failure of prior art pedicle screws to permanently attach to the vertebral body without loosening, pulling out, or causing vertebral fracture in substantially all cases, in accordance with one or more aspects of the present disclosure, a spinal bone shim attachment device adapted for engaging a pedicle screw to help avoid breaking out of the screw in the spinal bone during installation and use, is disclosed. Embodiments of the present disclosure provide a device which increases the surface area interaction between the pedicle screw and the cortical bone in order to provide a permanent attachment of the screw to the bone, necessary to improve both short-term and long-term patient outcomes. In addition, embodiments of the present disclosure also provide a device which assists a surgeon in the placement of a bone screw, including in cases where there has been an improper receiving channel, or tract, formed which presents a high risk of complications to the patient.

An embodiment of the present disclosure comprises a spinal bone shim attachment device adapted for use unilaterally with and engaging a pedicle screw to improve patient outcomes by preventing the breaking out of the screw in a spinal bone during installation and use of the shim attachment device and screw. The device comprises an elongated and partial shaft portion (an outer surface of which may be rounded or faceted in a cross-section view), having a base end and a tip end, the partial shaft portion being greater than 90 degrees but less than 270 degrees around when viewed in cross section, a base portion connected with the base end of the partial shaft greater than 90 degrees but less than 270 degrees around when viewed in cross section, a longitudinally extending concave surface within the shaft adapted for engaging the pedicle screw during use, an asymmetric tip positioned opposite the base portion and connected with the tip end of the partial shaft, and a plurality of bone engaging ridges extending outwardly from and along at least a portion of the length of the shaft, wherein the partial shaft portion, the base portion, and the tip, serve to guide the shim attachment device, and a subsequently installed screw, into a proper location while helping avoid the screw from breaking out of the spinal bone. The device may be composed of a compatible biomaterial, including a polymer such as Polyether-ether-ketone (PEEK). The partial shaft portion may be octagonal, cylindrical, or ovoid in shape, or may be in the shape of another polygonal prism.

The plurality of bone engaging ridges on the device each may comprise a first edge positioned normal to the partial shaft and extends outwardly from the partial shaft, and a second edge that is generally oriented at an angle relative to the partial shaft and connects the first edge to the partial shaft. Further, the plurality of bone engaging ridges may comprise a flat bottom edge, and the second edge may comprise a curve defined by an arc. Still further, the second curved edge and the first flat bottom edge may intersect at approximately a 90-degree angle at a location away from the partial shaft portion. The plurality of bone engaging ridges may be equidistant from one another, and there may be between 20 and 40 bone engaging ridges. In a particular embodiment, there may be 32 bone engaging ridges. The number of bone engaging ridges in a particular embodiment, however, will depend on the size of the ridges and the length of the device, and may vary.

The tip of the device may comprise a bias element for guiding proper placement of the shim attachment device and the screw into the spinal bone (vertebral body, cortical surface, pedicle, etc.). The bias element may comprise an enhanced angled outer surface of the tip surface relative to the elongated partial shaft portion and adapted for enhanced guiding of the spinal bone shim attachment device and the screw to proper placement during installation. The tip may further comprise an edge, and wherein the partial shaft portion further comprises an edge continuing from the edge of the tip, adapted for enhanced guiding and slicing as the tip and the partial shaft portion pass through flesh and bone.

The device may also comprise an asymmetric tip which is partially pyramid-shaped and further comprises a point at a leading end of the tip, a plurality of symmetrical slanted and longitudinally intersecting flat surfaces extending rearwardly and inwardly from the point and toward a longitudinal axis of the tip, a base surface at the tip end of the partial shaft portion and substantially normal to the plurality of intersecting flat surfaces of the tip, and an outer curved surface opposite the plurality of symmetrical slanted flat surfaces and which connects at outer longitudinally-extending edges of the plurality of slanted flat surfaces ending at the point. The base surface of the tip may be positioned substantially normal to the longitudinal axis of the tip and may intersect with the plurality of symmetrical slanted flat surfaces, the base surface being adapted for engaging the tip of the pedicle screw.

The concave surface within the partial shaft of the device may further comprise a plurality of guide channels adapted for engaging the pedicle screw. Each plurality of guide channels may have a longitudinally extending ridge which runs parallel to the partial shaft along the length of partial shaft. In a particular embodiment, there may be 4 guide channels defined by 3 longitudinally extending ridges. In an embodiment, the spinal bone shim attachment device adapted for engaging a pedicle screw may be a component of an intervertebral stabilization system comprising a plurality of pedicle screws, an intervertebral stabilization element coupling at least two adjacent pedicle screws anchored to an adjacent vertebra, a plurality of spinal bone shim attachment devices, one such device for each pedicle screw, each device comprising: an elongated partial shaft greater than 90 degrees but less than 270 degrees around when viewed in cross section and adapted for being positioned unilaterally alongside and guiding a pedicle screw; a base portion greater than 90 degrees but less than 270 degrees around when viewed in cross section and adapted for being positioned unilaterally alongside and guiding a pedicle screw; a concave inner surface within said partial shaft portion and adapted for engaging the pedicle screw; an asymmetric edged tip on the partial shaft portion and positioned opposite said base portion; and a plurality of bone engaging ridges extending away from the partial shaft portion and positioned along the longitudinally extending length of the partial shaft portion. Each such spinal bone shim attachment device is adapted to be inserted through a pedicle into a vertebral body with an exterior surface of the device facing away from the spinal cord, with the concave inner surface of the device facing towards the spinal cord, and where each the pedicle screw is inserted coextensive with the partial shaft portion of each spinal bone shim attachment device.

Thus, in accordance with one or more aspects of the disclosure, there is provided a spinal bone shim attachment device that may be thought of as a biased introducer to facilitate accurate pedicle screw placement. Such a shim may be used to augment bone screw fixation, particularly when there has occurred a failure of a receiving channel, or tract, placement or a stripped prior installation attempt. Therefore, the claimed spinal bone shim attachment device may be thought of as a device to reconstruct cortical bone margins in cases of a breech of the same.

In accordance with an aspect of the disclosure, there is provided a method for improving patient outcomes in spinal fusion surgery using the spinal bone shim attachment device of present embodiments. The preferred steps of the method comprise: providing a pedicle screw, providing a spinal bone shim attachment device adapted for guiding and engaging the pedicle screw, making an incision with a piercing member creating a pilot track extending from the skin surface of a patient through the pedicle and into the vertebral body, preparing the incision for the insertion of the spinal bone shim attachment device, inserting the spinal bone shim attachment device with a handle adapted for inserting the device and through the pedicle into the vertebral body with the outer surface of the device facing away from the spinal cord, and with the concave inner surface of the device facing towards the spinal cord, and inserting the pedicle screw into the pilot track adjacent and between the spinal bone shim attachment device and the spinal cord. The handle used to hold and insert the device may be comprised of a stainless releasable clamping device adapted to allow for applying necessary force to insert the device into the receiving channel, or tract.

With this improved method, surgeons are enabled in more consistently achieving successful placement of vertebral pedicle screws into spine bones of patients, and this, in turn, would lead to improved patient outcomes.

In accordance with another aspect of the disclosure, there is provided a method for improving patient outcomes in spinal fusion surgery following an improperly-angled incision in a patient which would likely result in screw mispositioning, using the spinal bone shim attachment device of present embodiments, is also disclosed. The method preferably comprises providing a pedicle screw, providing a spinal bone shim attachment device adapted for guiding and engaging the pedicle screw, making a proper incision at a correct angle with a piercing member creating a pilot track relative to a previously-made improper-angle incision and extending from the skin surface of the patient through the pedicle into the vertebral body, preparing the proper incision for the insertion of the spinal bone shim attachment device, inserting the spinal bone shim attachment device through the proper incision, through the pedicle, and into the vertebral body with the outer surface of the device facing away from the spinal cord, and with the concave inner surface of the device facing towards the spinal cord, with the spinal bone shim attachment device covering an entryway into the improper incision, and inserting the pedicle screw into the pilot track adjacent and between the spinal bone shim attachment device and the spinal cord. In this manner, the device may function as a "screw rescue" device and improve patient outcomes by covering the improper incision with the partial shaft of the device, and provide a surface for the threads of the pedicle screw to engage with, while still maintaining adequate engagement between the device and the vertebral body necessary to prevent loosening of the pedicle screw and associated complications.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings. For sake of consistency and ease of interpretation, the drawing views below are referenced to human anatomy in all cases, both where human anatomy is depicted and in reference to the preferred placement of a spinal bone shim attachment device within human anatomy (whether human anatomy is otherwise depicted or not). Thus, in those cases where human spine or back portions are depicted, reference to top, bottom, front, back, and side, each refer to such positions as one would normally consider referencing the human body (e.g., with the stomach side being the front (anterior), and the back side being the back (posterior)). And in those cases where a spinal bone shim attachment device is depicted itself, alone, without any part of the human body being referenced, a similar reference is used according to how the device would be placed in a human body generally speaking. Thus, views of an elongated longitude of the device will be considered side views generally, as the device would be viewed as generally elongated as viewed from a human being's side. Thus, it will be appreciated that a back view of the spinal bone shim attachment device are considered from the perspective of a human back (referencing normal placement of the device in a human spine), whereas side and top views of the device are considered relative to the most likely placement of the device in a human body as well, from the side (side view) and head (top view), respectively.

BRIEF DESCRIPTIONS OF DRAWINGS

DETAILED DESCRIPTION

Prior art bone screws commonly used in a variety of skeletal surgeries, including vertebral pedicle screws used in spinal fusion surgeries, are prone to failure and present a significant risk of negative patient outcomes. Prior art pedicle screws are prone to failure because of inadequate surface area interaction between the hard-cortical bone surface of the bone and the screw. In response to some failures of prior art bone screws to facilitate positive patient outcomes, and especially where an improperly angled receiving channel, or tract, for a bone screw has been created, an attachment device for facilitating the correct placement of a bone screw, with improved attachment between the patient's bone and the bone screw, is disclosed.

Figure 1:
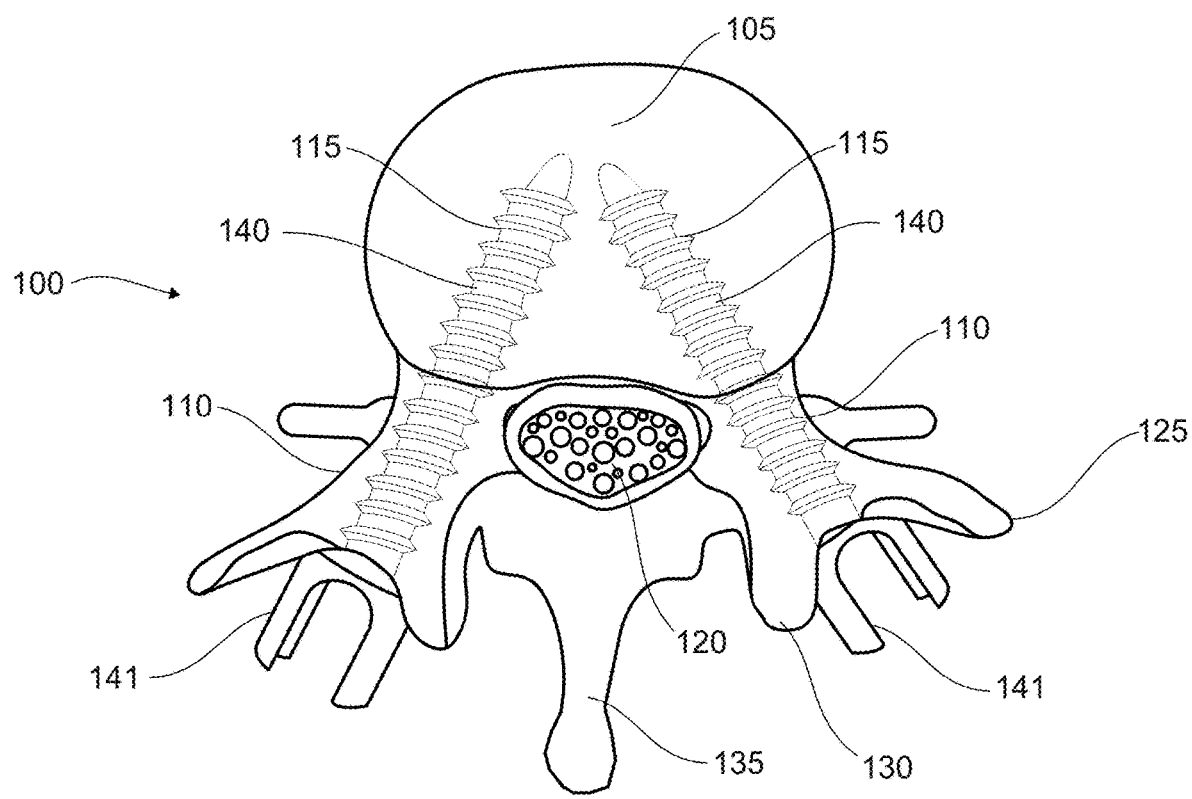
FIG. 1 shows a lateral cross-section top view of a thoracic vertebra and how two pedicle screws would be properly inserted into the vertebra, as set forth within the prior art.

FIG. 1 shows a cross-section view of a thoracic spine portion 100 with prior art pedicle screws 140 inserted into a region of the spine. The pedicle screws are inserted through the vertebral pedicle 110 and into the vertebral body 105, with the threads 115 of the screws engaging the hard-cortical bone along pedicles, and cortical rim surrounding the vertebral body 105. While the pedicle screws will also engage the cancellous bone within the vertebral body, it is the narrowed cortical bone portion of the pedicle which bears most of the load applied to the spine, and which will bear most of the load applied by the pedicle screws. Depending on the location of the spine in which the screw is inserted, there may be a transverse process 125, an articular process 130, and a spinous process 135 near the base of the screw.

When placing the pedicle screws 140, it is critically important to create a receiving channel, or tract, as with a piercing tool, that goes through the center of the pedicle bone 110 and into the center mass of the vertebral body 105, and which does not pass through the spinal cord 120. Damage to the spinal cord 120 results from screw placement angled too close to the center of the spine, and this may lead to nerve injury resulting in paralysis of the patient. Improper screw placement can also result from a receiving channel which is formed at an angle which places the screw too far to the edge of the pedicle and places the screw at a location away from the center mass of the vertebral body (e.g., as shown by receiving channel 703 shown in FIG. 7). Such improper placement of a screw 140 at too wide an angle not passing through the center of the pedicle 110 and into the center mass of the vertebral body 105 must be re-created and the screw re-placed in order to ensure a positive patient outcome.

Figure 2:
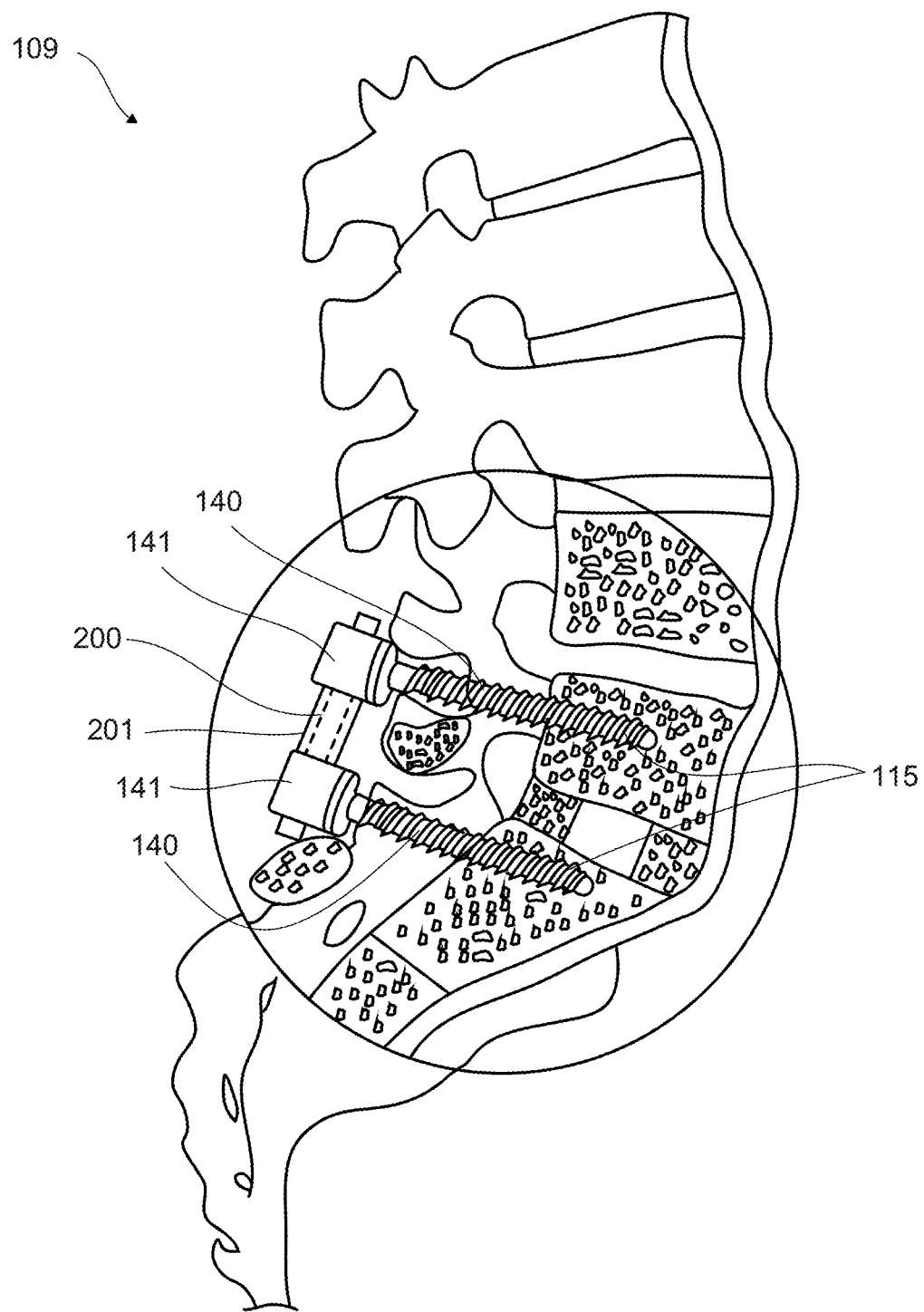
FIG. 2 shows a longitudinal partial cross-section side view of the lumbar spine and how two pedicle screws would be properly inserted into the vertebrae and bound together as a part of an intervertebral stabilization system, as set forth within the prior art.

FIG. 2 shows a longitudinal cross-section side view of the lumbar spine 109 with two prior art pedicle screws 140 properly inserted and bound together as a part of an intervertebral stabilization system. The pedicle screws 140 are inserted through the pedicle 110 and into the vertebral body 105, with the threads 115 primarily engaging an inner cortical surface of the pedicle bone. Following proper insertion of a pedicle screw 140 as part of an intervertebral stabilization system, cross members 200 (i.e., known as cords, and with spacers 201 between heads 141 of the pedicle screws 140) connecting the various pedicle screw heads 141 to immobilize the vertebrae and allow for a successful vertebral fusion at the location of the intervertebral stabilization system.

Figure 3A:
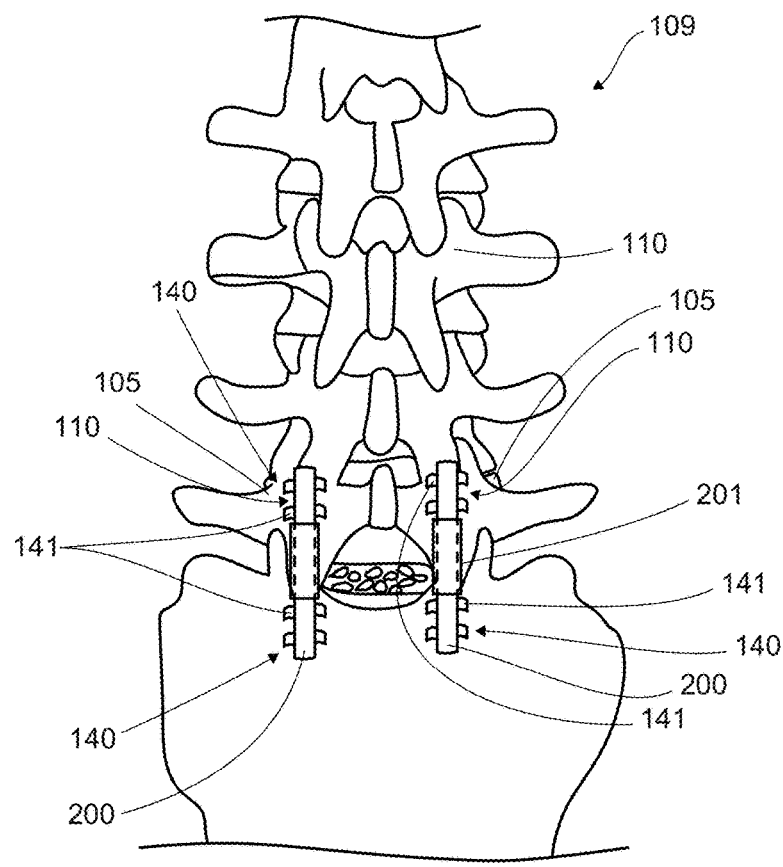
FIG. 3A shows a posterior, or back, view of a lumber spine and how four pedicle screws would be inserted into the vertebrae and bound to each other on the right and left side of the spine as a part of an intervertebral stabilization system, as set forth within the prior art.
Figure 3B:
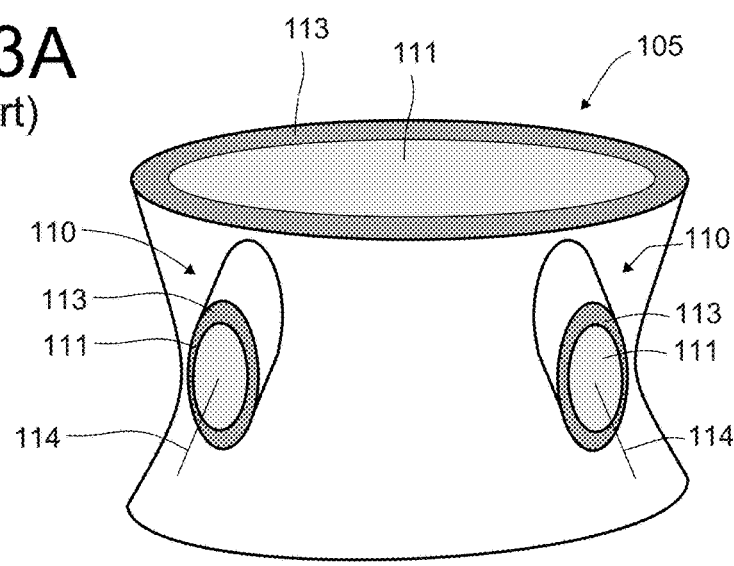
FIG. 3B shows a representative diagram of a mostly posterior, or back view, of a lumbar thoracic vertebra further indicating an oblong oval cross-section shape and axis of pedicles through which pedicle screws pass during a vertebral stabilization process.

FIG. 3A shows a back view of a lumbar spine 109 with four prior art pedicle screws 140 inserted and bound to each other with cross members 200 and spacers 201 on the right and left side of the spine as a part of an intervertebral stabilization system. The pedicle screws 140 are inserted through the pedicle 110 and into the vertebral body 105 (see FIGS. 1 and 2 for further reference), with the threads 115 (FIGS. 1 and 2) engaging the inner cortical surface of the pedicle 110. FIG. 3B shows a representative diagram of a mostly posterior, or back view, of a lumbar thoracic vertebral body 105, further indicating a typical oblong oval cross-section shape and pedicle longitudinal axis 114 of the pedicles 110 and inner cancellous (softer) bone 111 through which pedicle screws pass during a vertebral stabilization process, whereas cortical (harder) bone 113 of the pedicle and vertebral body are also indicated. Because of this structure of pedicles 110, prior art vertebral stabilization pedicle screws have not always had sufficient engagement to cortical bone 113, and therefore some have loosened over time.

Figure 4A:
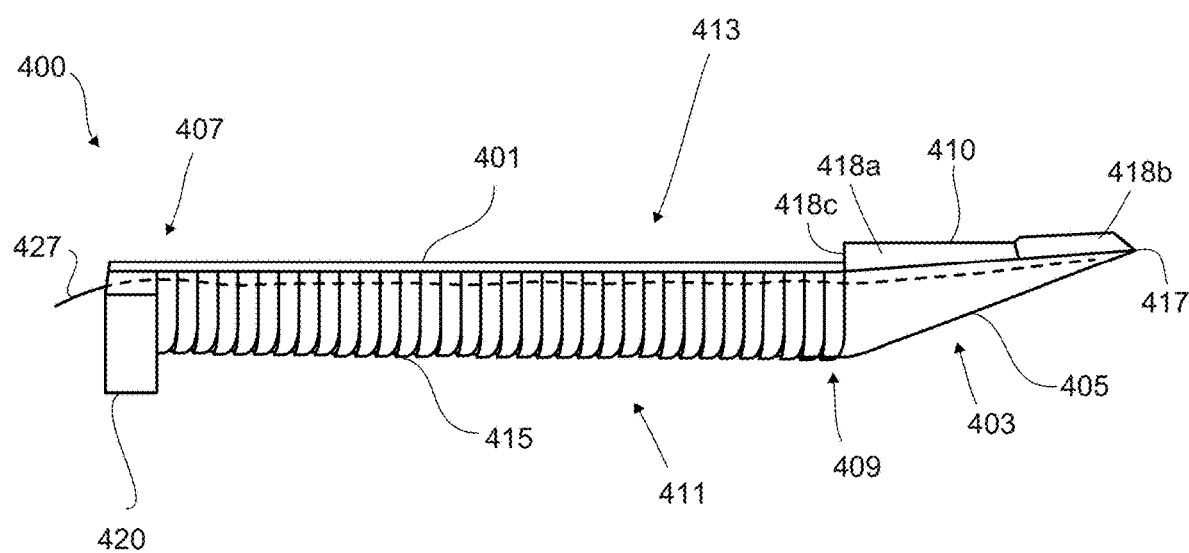
FIG. 4A shows a longitudinal side view of an embodiment of a spinal bone shim attachment device in accordance with one or more aspects of the disclosure.
Figure 4B:
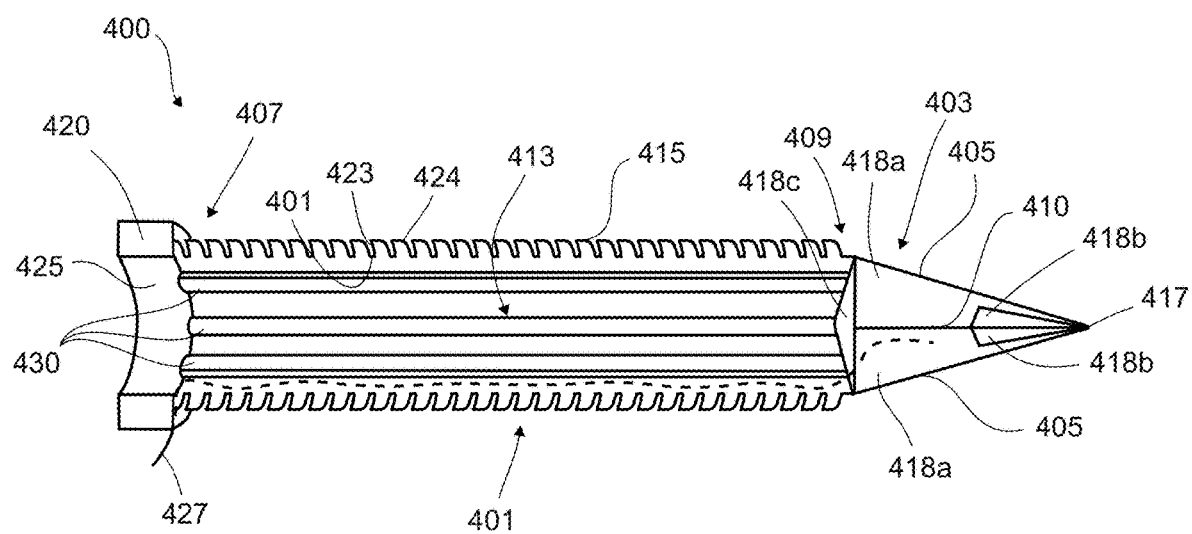
FIG. 4B shows a longitudinal right-side view (considering placement of the device on the right side of a person's spine as viewed from their front) of the spinal bone shim attachment device of FIG. 4A.
Figure 4C:
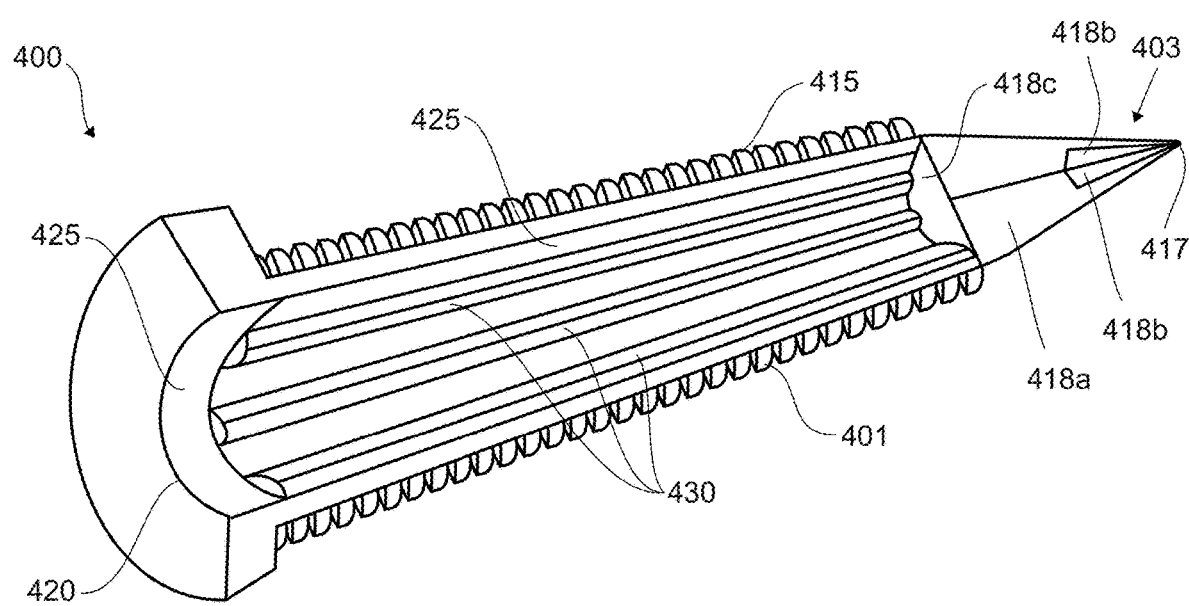
FIG. 4C shows a perspective top right-side view of the spinal bone shim attachment device of FIG. 4A.

Referring to FIGS. 4A-4C, there is shown a preferred embodiment of a spinal bone shim attachment device 400 in accordance with one or more aspects of the disclosure. The device 400 comprises a partial shaft 401, partial in the sense that it is greater than 90 degrees but less than 270 degrees around in transverse cross section relative to the longitudinal axis of the device 400. The device 400 also comprises a partial semicircular, partial ovoid or partial polygonal shaped base 420 at a first end 407 of the partial shaft 401, and an asymmetric tip 403 at a second end 409 of the partial shaft. The partial shaft 401 therefore runs most of the length of the device 400, between the base 420 and the asymmetric tip 403. The tip 403 is slanted inwardly, as with a biased taper 405 at a tip portion of an exterior side 411 of the device 400, and there is an internal straight edge 410 at a tip portion of an interior side 413 of the device. Further, there may be provided a plurality of faceted surfaces 418a, 418b, 418c at the tip portion on the interior side 413 of the device 400, to facilitate with guiding the device through tissue and providing for enhanced structural strength of the device.

The device 400 further comprises an exterior (in the sense of exterior of the device 400 relative to a spinal cord 120) surface 415 running most of the length of the device, generally comprised of a plurality of bone engaging ridges, or knurling, 415. The shim device 400 further comprises a plurality of interior longitudinally extending ridges 430 located along the inner surface 413 of the device, where the ridges are adapted to interact with a bone screw 140.

The partial shaft 401 of the device 400 may come in a variety of length and width sizes to accommodate placement of bone screws in a variety of locations (e.g. hip, knee, spine) and for patients of various size with differing anatomy and bone structure. A non-exhaustive range of possible dimensions (overall width and length) for the device 400 may include the range of approximately 3.5 mm×20 mm to 9.5 mm×60 mm. The partial shaft 401 and partial base 420 cross-section shape may be partial circular, partial ovoid, or they may be in the shape of a partial polygonal prism, such as a partial octagonal prism. The device 400 and the partial shaft 401 are unilateral in their construction, only being continuous around a portion of the cross-section circumference of the device, and preferably having an asymmetric biased tip 403 to aid guiding the device 400 to a proper location within the spine and as aided by guide channels 701. Optimal angles of extent, as viewed in cross section, for the partial shaft 401 and partial base 420 are within a range of 90 to 270 degrees and may include angles of approximately 120 and 150 degrees. The partial shaft 401 is preferably concave along its length to be able to adequately guide and engage a pedicle screw 140 as it is placed in a receiving channel, or pilot track, 701 created in a patient's spine.

The tip 403 may be asymmetrically biased, or pointed (as at 417), with slanted exterior edges, such as a biased taper 405, which intersect with an interior straight edge 410 along the interior, or inner, surface 413 of the device 401 at the tip 403. The tip 403 ends in a point 417 adapted for easy insertion through a properly formed receiving channel 701 (see FIG. 5).

A properly created receiving channel 701 will be angled between the spinal cord 120 and the transverse process 125, and preferably it passes through the center mass of the pedicle bone 110 and into the vertebral body 105. The bias portion, or element, 405, 418b, is adapted for guiding proper placement of the shim attachment device 400 and the screw 140 into the pedicle bone 110 through a properly created receiving channel 701. The bias element 405, 418b thus guides the tip 403 of the shim device 400 into the bone (e.g., pedicle bone 110), and the faceted point 418b formed at the intersection of the bias element 405 and the internal straight edge 410 on the interior surface 413 of the device 400 further serves to guide the device 400 within the correctly formed receiving channel 701.

The faceted point 418b may be adapted to push through bone, and in particular cancellous bone, within the spine. The faceted point may be 1 to 1.5 cm in length, and the overall tip (including the faceted point) is preferably about 2.0 cm in length, as to allow for the ridged or knurled partial shaft 415 to be long enough to maximize interaction with the cortical bone. The tip 403 may be a partial pyramid shape, and can be further characterized by a flat interior base surface 418c (FIG. 4C) at an intersecting region at the second end 409 of the partial shaft 401 and the tip 403, which interior base surface is adapted for engaging the end of a bone screw 140. Further, the flat base surface 418c may serve to provide an additional anchor point for the end of the bone screw 140 to screw into, and it may thereby increase the surface area interaction between the bone screw and the device 400. In an alternative embodiment, it is possible that instead of a flat base surface 418c, there may be provided a conical- or a cone-shaped surface at the base of the tip and which may also therefore increase the surface area interaction between the end of the bone screw 140 and the device 400.

Alternatively, the tip 403 may also be provided with a gentle curve or an arc (at 405) on the exterior edge of the tip 403, and which runs the length of the tip and ends in a simple, or faceted, point 417. In such an embodiment, the gentle curve which makes up the exterior edge of the tip may be partially circular in cross-section shape and may resemble a partial circle in cross section, and as the cross section is taken further and further along the tip approaching the point 417, the cross section partial circle decreasing in size until it ends in a point 417. It will be appreciated that a variety of cross-section shapes may be used to create a tip 403 which engages the spinal bone and pierces through the pedicle 110 (via a receiving channel 701) and into the vertebral body 105, the tip not being limited to the shapes shown in FIGS. 4A-4C or described herein.

The plurality of bone engaging ridges 415 are adapted to engage and secure attachment between the bone screw 140 and the pedicle bone 110. The bone engaging ridges 415 in particular may be adapted to engage the cortical surface of the pedicle bone 110 and cortical rim of the vertebral body 105 as to facilitate a strong attachment between a pedicle screw 140 inserted into the shim device 400 and spinal bones. In an embodiment, the exterior bone engaging ridges, 415 comprise an edge, or surface, 423 extending away from the partial shaft 401 (i.e., forming an angle up to 90 degrees with the partial shaft) and which bends approximately at a 90-degree angle and extends as another edge, or somewhat concave curved surface, 424 along a line before curving back down to the base as shown in FIGS. 4A and 4B. Thus, each bone engaging ridge 415 may appear in cross section (i.e., a longitudinally oriented plane relative to the longitudinal length of the device 400) basically as a sawtooth, yet preferably each bone engaging ridge 415 also extends as a circumferential ridge extending from and around the outer portion 411 of the partial shaft 401.

The 90-degree edge of each bone engaging ridge 415 may thus be placed substantially normal to and against the surface of the pedicle bone as the device 400 is inserted into the receiving channel 701 and a pedicle screw is inserted into the device, causing displacement of the partial shaft 401, and compression of the bone engaging ridges 415 against the pedicle's 110 inner cortical bone. Described differently, the or bone engaging ridges 415, may slope downwardly for each course of ridges 415, and then cut back in at a perpendicular angle relative to the main body of the shim device 400, so as to be adapted to "bite" into the bone 110 and facilitate maximum interaction and engagement with the bone surface.

Figure 4D:
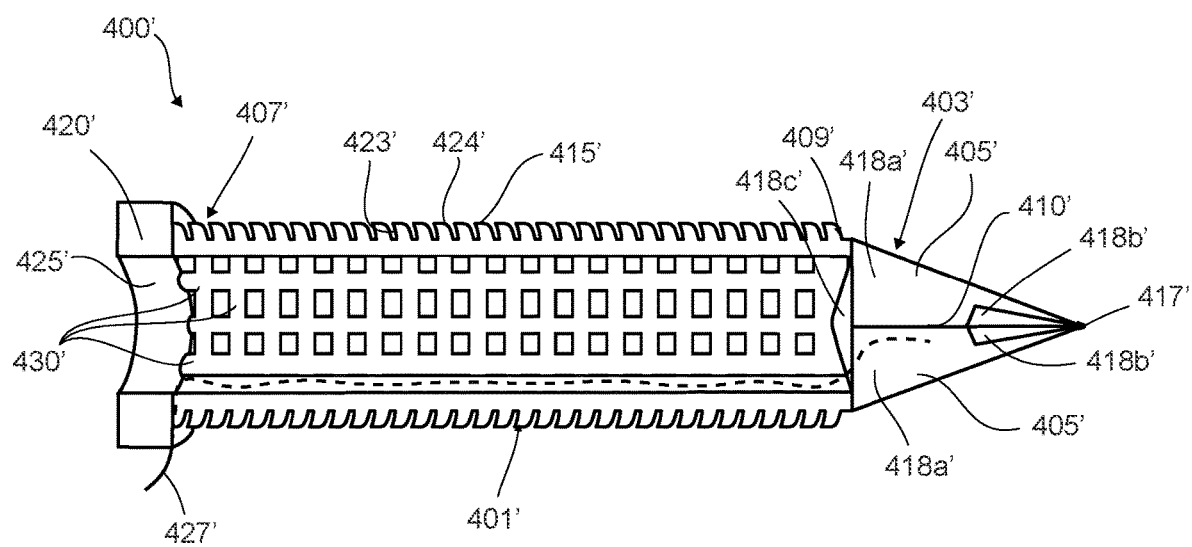
FIG. 4D shows a closeup view of an alternative screw engaging knurling, ridges, or lattice-type structure, for an alternative spinal bone shim attachment device.
Figure 5:
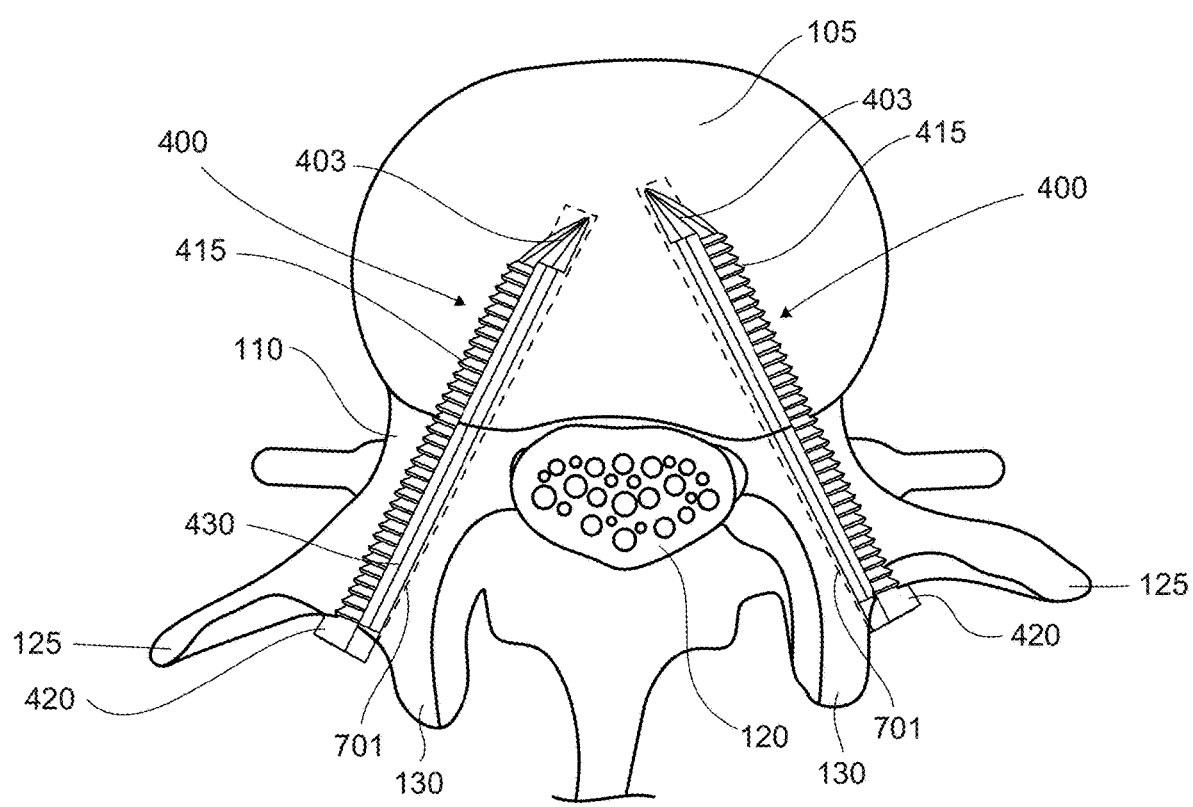
FIG. 5 shows a lateral cross-section top view of a thoracic vertebra and how two alternative spinal bone shim attachment devices would be inserted into two properly placed incisions in the vertebra.

Alternatively, there are provided a plurality of alternative bone engaging ridges 415', wherein each bone engaging ridge as shown in FIG. 5 may comprise a first edge (or convex slightly curved surface) 423' starting positioned normal to the shaft 401 which extends outwardly from the shaft, and a second edge (or surface) 424' which is generally oriented at an angle (e.g., around 45 degrees, more or less) relative to the partial shaft 401 and connects the first edge to the partial shaft in (as shown in in FIG. 5). However, a variety of patterns and shapes may be used to create the bone engaging ridges 415, 415' which engage the spinal bone, and the exterior bone engaging ridges are not limited to the shapes and patterns shown in FIGS. 4A-8 or described herein.

FIG. 4B shows an interior view of the spinal bone shim attachment device 400. Shown along the interior face 413 of the device 400 is the inside portion 413 of the partial shaft 401 with the exterior bone engaging ridges 415 continuously running along the exterior face of the device from the beginning of the partial shaft on the first end 407 of the device, to the second end 409 of the partial shaft at the beginning of the tip 403. Also shown is the interior face of the tip 403 which may comprise slanted edges 405 (i.e., cutting edges) along the outside lateral surfaces of the device 400, with an edge 410 (or ridge) bisecting the slanted edges.

The interior screw engaging ridges 430 on the concave inner surface 425 of the device 400 preferably comprise a series of raised parallel ridges 430 which preferably run longitudinally the length of the partial shaft 401. These raised ridges 430 contact a bone screw 140 along the threads 115 of the screw in order to provide an enhanced engagement area to facilitate attachment of the screw to the shim device 400. Thus, there will be increased pressure along the ridges 430 at the points where they contact the screw threads 115 due to the reduced surface area of the ridges relative to a flat surface, and this high-pressure compression facilitates improved attachment between the screw and the shim device 400, since the screw threads are seen as thus better able to cut into and thus engage the ridges 430 than they would with just a flat, or simply curved, surface area on the interior of the device 400.

In FIG. 4D there is provided an alternative pattern of screw engaging ridges 430', wherein there are a secondary series of parallel ridges which are perpendicular to the first series of ridges 430', and which run around the interior circumference of the device 400'. In such an alternative embodiment, a grid of raised ridges 430' is formed by the intersecting perpendicular raised ridges, and these will contact the threads 115 of the screw 140 at multiple different angles, and from different sides. This will provide a compressive force against the screw in multiple different directions, and thus, the perpendicular raised ridges 430' may facilitate increased attachment between the screw 140 and the device 400' by better locking it into place and preventing screw motion following insertion of the screw due to the compressive force applied to the screw by the intersecting perpendicular raised ridges. This, in turn, allows the screw threads to penetrate the grid cavities created by the perpendicular raised ridges 430'. Thus, the design of the raised ridges 430', as shown and described herein, creates an enhanced surface area to contact the threads 115 of a bone screw 140, but does so in a manner which does not compromise the strength of the body of the device 400'. This may be done by adding the ridges 430' on top of the initial thickness of the shaft 401', and this may serve to increase the strength of the partial shaft 401' by providing additional structural support for the body of the shaft. Similarly to the spinal bone shim attachment device 400 of FIG. 4B, the final bone shim attachment device $_4$00' of FIG. 4D likewise comprises a base $_4$20', a concave inner surface 425', first and second ends, 407', 409', a wire tracer 427', faceted surfaces 418a-c' (wherein 418c' comprises a flat interior base surface), an asymmetric tip 403', a biased taper 405' at a tip portion of the device, an internal straight edge 410', and a pointed tip 417'.

Thus, it will be appreciated by those skilled in the art that the interior screw engaging ridges 430, 430' may have different patterns, and while particular embodiments of the interior screw engaging ridges 430, 430' are set forth above, a variety of patterns and shapes may be used to create the interior ridges which engage the bone screw 140, and the interior ridges are not limited to the shapes and patterns displayed in FIG. 4B, 5, or otherwise described herein.

Additionally, the device 400 may further comprise a wire tracer 427 as shown in FIG. 4C which runs the length of the device along the shaft, or a wire mesh fabricated coextensive with the surface of, or implanted within, the device as to allow for visualization of the device with medical imaging, and in particular visualization using x-ray imaging.

FIG. 4C shows a perspective view of the spinal bone shim attachment device 400. Shown in this view are the partial base 420, the unilateral partial shaft 401, the exterior bone engaging ridges 415, the concave interior 425 of the device, the interior screw engaging ridges 430 in the embodiment of raised parallel ridges, the tip surface 418c at the second end 209 of the intersection of the partial shaft 401 and the tip 403, and the asymmetric tip 403 further comprising surfaces 418a and 418b and point 417. FIG. 5 shows a lateral cross-section view of a thoracic vertebra with two of the spinal bone shim attachment devices 400 inserted into two properly placed incisions 701. The spinal bone shim attachment devices 400 are inserted through the pedicles 110 and into the vertebral body 105, with the asymmetric tips 403 inserted deep into the inner cancellous bone of the vertebral body. The exterior bone engaging ridges 415 engage the hard weight bearing cortical bone along the pedicle no and cortical rim surrounding the vertebral body 105. The device 400 is inserted at an angle through the center of the pedicle 110, away from the spinal cord 120, between the transverse process 125 (which protrudes from the pedicle) and the spinous process 130 (which protrudes from the center mass of the spine). Also pictured is the interior screw engaging ridges 430 in the concave inner surface of the device for engaging the bone screw 140.

Figure 6:
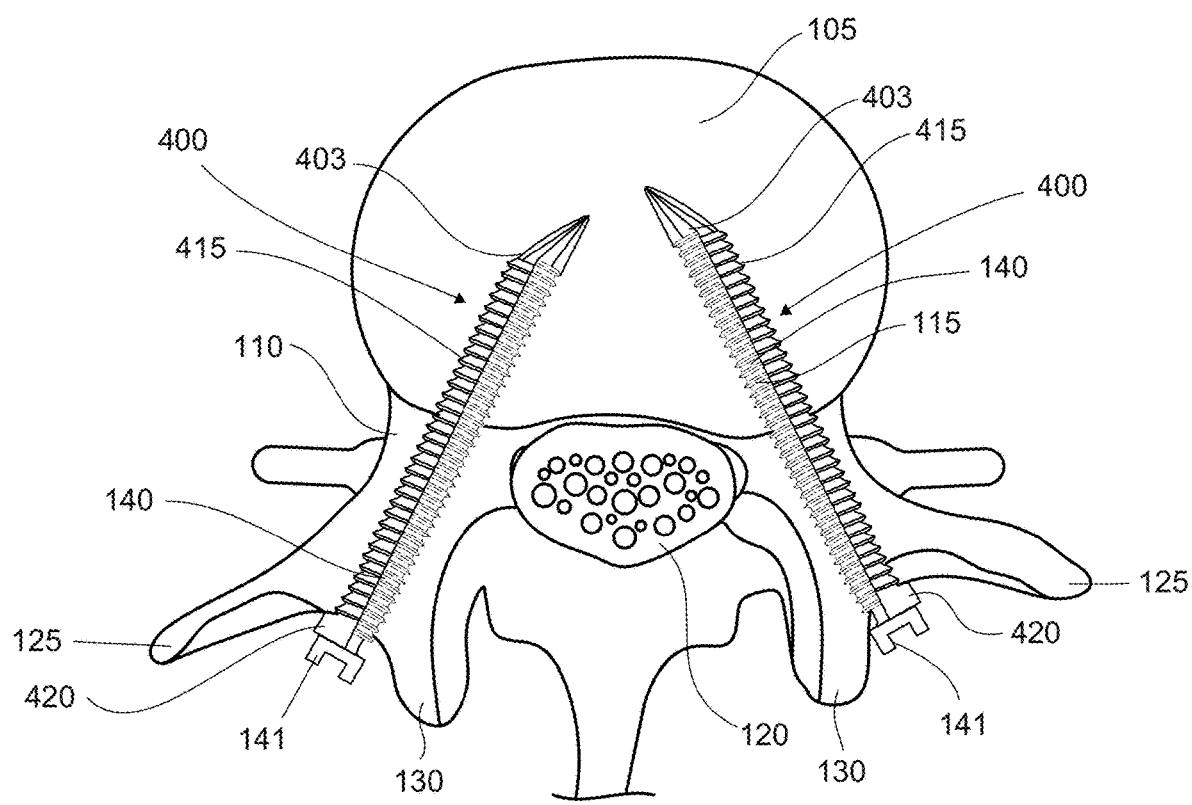
FIG. 6 shows a lateral cross-section top view of a thoracic vertebra and how two of the alternative spinal bone shim attachment devices of FIG. 5 would be inserted into two properly placed incisions in the vertebra, and with a pedicle screw inserted into each device.

FIG. 6 shows a lateral cross-section view of a thoracic vertebra with two of the spinal bone shim attachment devices 400 inserted into two properly placed incisions and with pedicle screws 140 inserted into each device. The pedicle screw 140 is inserted into the device 400 along the unilateral partial shaft 401. The device 400 is inserted through what amounts to a pilot hole 701 in the center of the pedicle 110 and into the center mass of the vertebral body 105. The asymmetric tip 403 of the device 400 is pushed through the bone and guides the placement of the device. The device 400 is inserted at an angle away from the spinal cord 120 and away from transverse process 125 which protrudes from the pedicle, and through the center of the pedicle 110. The threads of the bone screws 115 will engage with the interior raised longitudinal ridges 430 of the device 400 (see FIG. 6) to facilitate an improved interaction between the device and the bone screw 140. The exterior bone engaging ridges 415 provide additional surface area in a shape designed to maximize the pressure placed upon the bone at the places where the bone engaging ridges engage hard cortical bone. Thus, the bone engaging ridges 415 engage with the cortical surface of the bone to facilitate improved attachment between the device 400 and the spinal bone.

Figure 7:
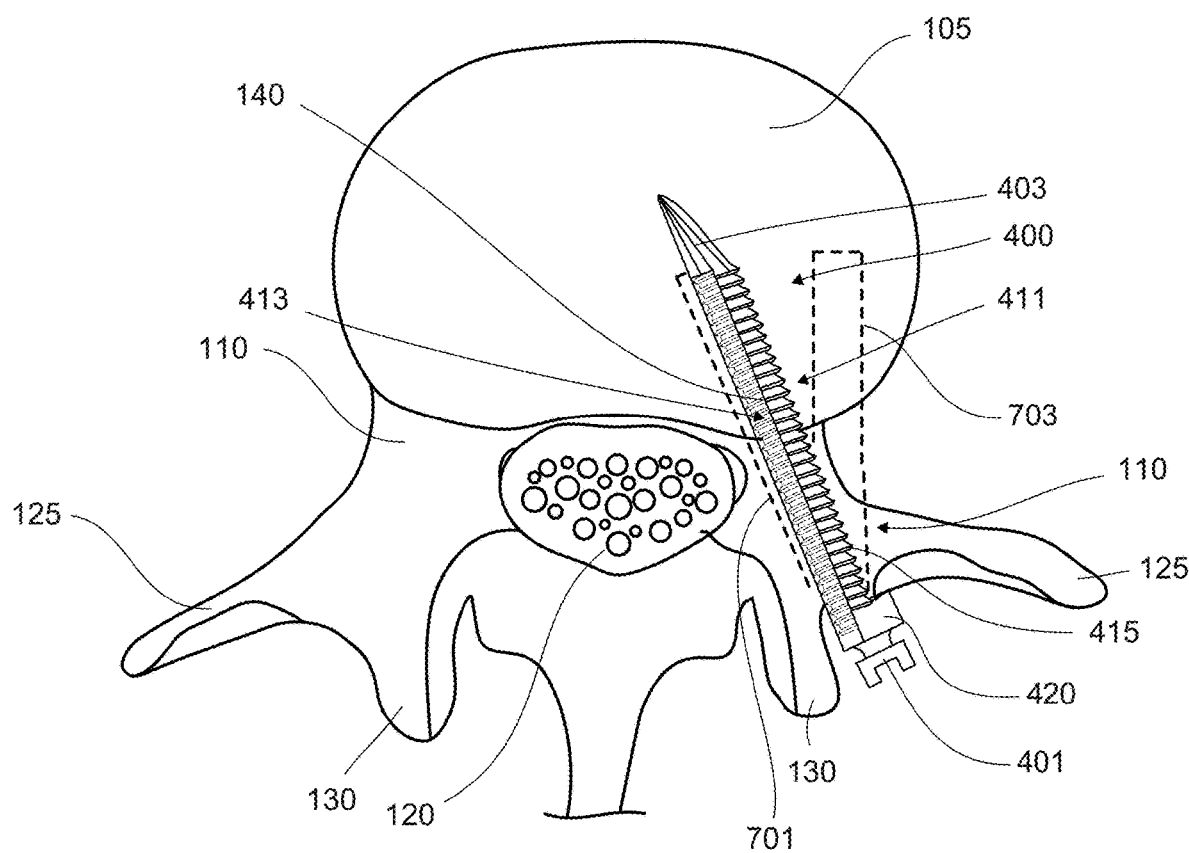
FIG. 7 shows a lateral cross-section top view of a thoracic vertebra and how an alternative spinal bone shim attachment device of FIG. 5 would be inserted properly into the vertebra to serve as a screw rescue relative to a previous improperly placed incision.

FIG. 7 shows a lateral cross-section view of a thoracic vertebra with a spinal bone shim attachment device 400 inserted properly in a properly placed incision 704 relative to an improperly placed incision 703. Similar to FIG. 6, The pedicle screw 140 is inserted into the device 400 along the partial shaft 401, the device is inserted through the incision, essentially a pilot hole, 701 through the center of the pedicle 110 and into the center mass of the vertebral body 105. Properly placed, the incision 701 is created at an angle away from the spinal cord 120 and away from transverse process 125 which protrudes from the pedicle. In this an embodiment of the shim device 400, the exterior face 411 of the partial shaft 401 faces outwardly away from the spinal cord 120 towards the transverse process 125 and covers access to the improperly placed incision 703. This allows for a pedicle screw 140 to easily be inserted into the correct incision 701 along the interior face 413 of the partial shaft 401, as there is no tendency for the screw to follow the path of the improperly formed incision 703 due to the improper incision being covered by the shim device 400.

Figure 8:
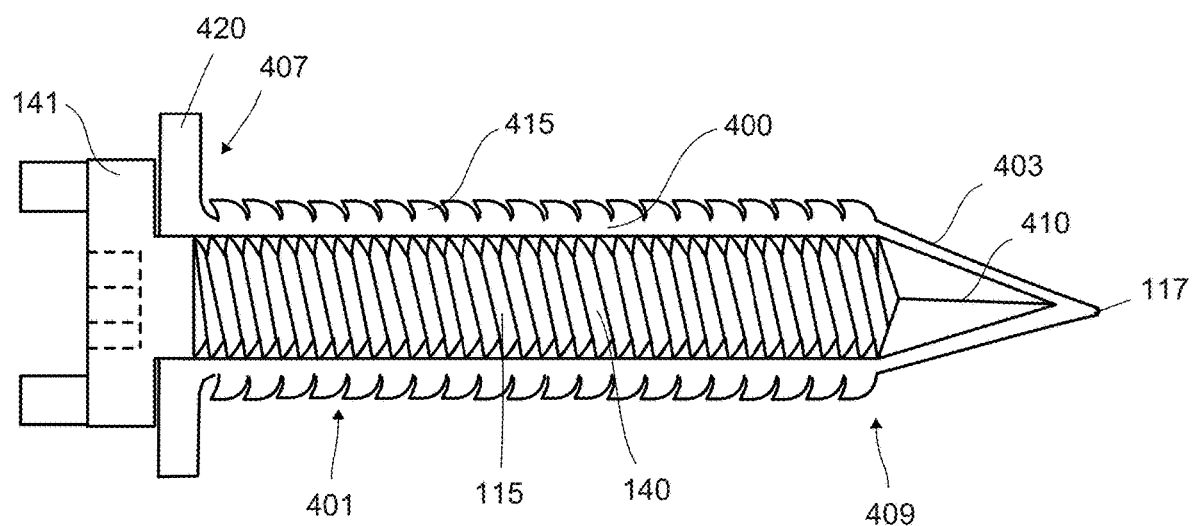
FIG. 8 shows a right-side view (considering placement of the device on the right side of a person's spine as viewed from their front) of a spinal bone shim attachment device together with a pedicle screw.

FIG. 8 shows a longitudinal side view of the spinal bone shim attachment device 400 of present embodiments with an inserted pedicle screw 140. Shown is the exterior knurling 415 which engages the bone, the asymmetric tip 403, the slanted exterior edges on the tip, the flat interior edge 410 of the tip 403, the partial shaft 401, the partial base 420, and the threads 115 of the screw 140 which engage the bone and interior concave surface of the partial shaft 401 and interior ridges 430, 430'. The pedicle screw 140 will displace the partial shaft 401 of the shim device 400, and cause the exterior bone engaging ridges 415 of the device to engage the bone at an enhanced angle relative to the position of the exterior ridge engagement without a pedicle screw. Similarly, the interior ridges 430 of the device will also engage the pedicle screw threads 115 at an enhanced angle due to the displacement of the partial shaft 401 caused by the insertion of the screw 140.

The spinal bone shim attachment devices 400, 400' may be composed of a variety of compatible biomaterials, such as Ti or PEEK (polyether ether ketone). However, it is desirable to select a biomaterial with an elastic modulus that is similar to that of bone as to resist being damaged by the bone tissue, while also not damaging the surrounding bone tissue. The elastic modulus of a material is a quantity that measures an object's resistance to being deformed when a stress is applied to it. The elastic modulus, also called Young's modulus, is defined as the slope of the stress-strain curve in the elastic deformation region of a material. A material is within the elastic deformation region where it is deformed without being permanently damaged or permanently changing in shape. If a material has an elastic modulus less than that of bone, then the load across the bone tissue will be primarily bore by the bone and not the biomaterial. Conversely if the elastic modulus is greater than that of bone, then the load will primarily be bore by the biomaterial. In particular PEEK is a suitable material for use with bone tissue because it has an elastic modulus of 3.6 GPa.

The average elastic modulus of cancellous bone measured ultrasonically has been reported to be 14.8 GPa, and reported to be 10.4 GPa when measured mechanically. J Y Rho, et al., *Young's Modulus of Trabecular and Cortical Bone Material: Ultrasonic and Microtensile Measurements,* 26(2) J. Biomechanics 111-119 (1993). The average elastic modulus of cortical bone measured ultrasonically has been reported to be 20.7 GPa, and reported to be 18.6 GPa when measured mechanically, and more broadly has been reported to be within the range of 7-30 GPa, as it may vary among patients. Id.; Amaral, M., Lopes, et al., *Densification route and mechanical properties of Si 3 N 4-bioglass biocomposites,* 23(3) Biomaterials 857-862 (2002).

Having an elastic modulus of 3.6 GPa, PEEK is therefore a compatible biomaterial with bone because its elastic modulus is high enough such that it can withstand the pressure placed upon it surrounding bone tissue following the placement of a pilot hole, without permanently damaging the biomaterial, while also not damaging the bone tissue. Since PEEK's elastic modulus of 3.6 GPa is less than that of bone as it has been reported broadly, it does not present a significant risk of damaging the surrounding bone tissue following insertion of the device in almost all patients, thereby making it a suitable biomaterial for use as spinal bone shim attachment devices 400, 400' with bone screws 140.

Ti is also a compatible biomaterial that has been used with some success across various applications in implants, including in bone screws. Despite having an elastic modulus of 113.8 GPa, it has been used with success in bone screws notwithstanding the risk of damaging surrounding bone tissue due to its strong resistance to deformation, evidenced by its high elastic modulus greater than that of bone. Accordingly, it may also be possible to produce the shim device of present embodiments with Ti.

Other important properties of biomaterials used to fabricate the spinal bone shim attachment devices 400, 400' include hardness, fracture strength, fracture toughness, and fatigue. It is desirable to fabricate the device 400, 400' out of a material with a hardness similar to that of bone, high resistance to fracture, and high resistance to material fatigue. PEEK is a suitable biomaterial for use in bone tissue because it has a hardness similar to that of bone, high resistance to fracture, high fracture toughness, and high resistance to material fatigue.

While particular embodiments of composition of the device 400, 400' are set forth above, a variety of compatible biomaterials may be used to create the device which engages the bone screw, and the composition of the device is not limited to the biomaterials disclosed herein.

The spinal bone shim attachment devices of present embodiments may be fabricated using a variety of different manufacturing techniques known within the art which are suitable for production of devices using biomaterials, including casting, molding, 3D printing, and other methods.

Also disclosed is a method of using the spinal bone shim attachment device 400, 400' of present embodiments with bone screws 140 generally and in spinal fusion surgeries. An improved method for the placement of bone screws 140 likely to reduce complications associated with various forms of screw failure which will improve patient outcomes is disclosed. An improved method for placement of bone screws may comprise:

providing a bone screw, providing a bone shim attachment device 400, 400' for coupling to a bone screw;

making an incision 701 into the bone with a piercing member, which may include a percussion drill designed for "drilling", or more properly forming, or piercing, bone, the incision extending from the surface of a patient's skin through the cortical bone and into the cancellous region of the bone;

preparing the incision 701 for the insertion of the shim attachment device 400, 400';

inserting the shim attachment device 400, 400' into the incision 701 at an orientation which will account for the displacement of the partial shaft 401, 401' and the associated compressive force placed on the bone in at least two opposing directions;

inserting the bone screw 140 into the shim device 400, 400'; and tightening the screw 140 and shim device 400, 400' into place as necessary.

In another embodiment, it may also be possible to preinsert the bone screw 140 into the shim device 400, 400', either partially or fully, before insertion into the bone tissue, and insert both the screw and shim device at the same time.

Also disclosed is a method of using the spinal bone shim attachment device 400, 400' as a screw rescue device to assist in the placement of bone screws, including pedicle screws, 140 in cases where there has been an improperly formed incision 703 into the bone. Similar to the method for improved method for the placement of bone screws 140 disclosed above, the method comprises:

providing a bone screw 140;

providing a bone shim attachment device 400, 400' for coupling to the bone screw 140;

making an incision 701 into the bone with a piercing member, which may include a percussion drill designed for "drilling", or more accurately piercing, bone, the incision extending from the surface of a patient's skin through the cortical bone and into the cancellous region of the bone; and preparing the incision for the insertion of the shim attachment device 400, 400'.

However, in the case of an improperly formed incision (e.g., incision 703 of FIG. 7), it is likely at the stage of preparing the incision that a surgeon may realize that the incision is angled improperly and must be redone in order to allow for proper placement of the bone screw 140. In this embodiment, the surgeon will then repeat the above steps comprising:

making an incision 701 into the bone with a piercing member, which may include a percussion drill designed for piercing bone, the incision extending from the surface of a patient's skin through the cortical bone and into the cancellous region of the bone;

preparing the incision for the insertion of the shim attachment device 400, 400';

once a properly angled incision 701 has been formed, the method will then comprise the added steps of inserting the shim attachment device 400, 400' into the incision at an orientation which will account for the improperly formed receiving channel, or tract, and into the proper receiving channel, or tract, with the exterior surface 411 of the partial shaft 401 of the shim device covering the improperly formed incision 703;

inserting the bone screw 140 into the shim device; and tightening the screw and shim device into place as necessary.

In this improved method, the shim device 400, 400' will prevent the bone screw 140 from interacting with the improperly formed incision 703, will cover the improperly formed incision 703, and will also facilitate the permanent fixation of the bone screw in its desired location due to the increased surface area interaction between the screw and the device, as well as the device and the cortical bone.

Figure 9:
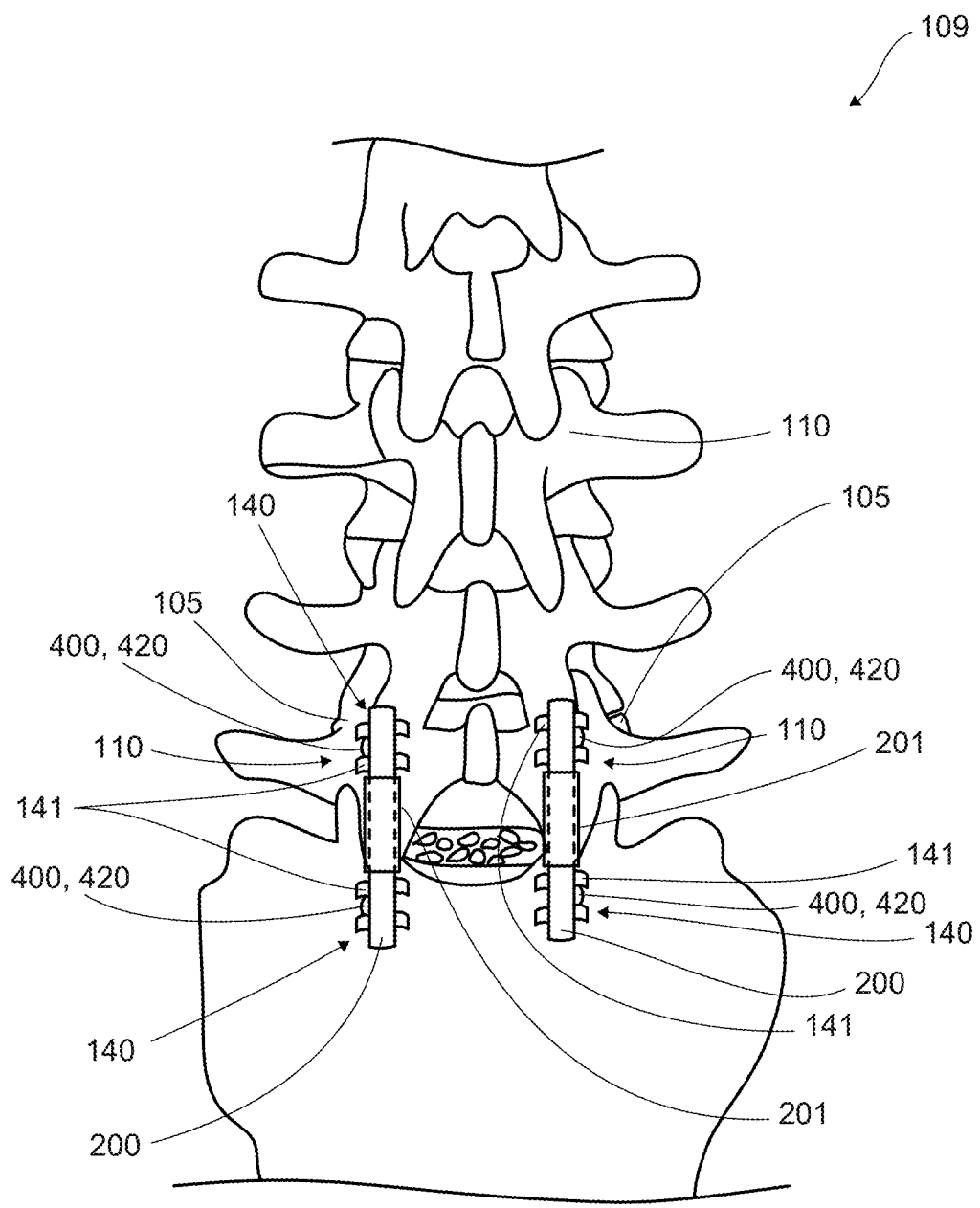
FIG. 9 shows a back view of a portion of a lumbar spine and how four spinal bone shim attachment devices in accordance with one or more aspects and an embodiment of the disclosure would be inserted having pedicle screws inserted into the devices and the spine as components of an intervertebral stabilization system.

When used as a screw rescue device in a spinal fusion surgery to facilitate an easier insertion, and permanent fixation, of a bone screw, it is possible the device 400 (or alternatively 400') may be used as components of an intervertebral stabilization system as shown in FIG. 9. In such an embodiment, the shim device 400 will facilitate increased attachment between the pedicle screw 140 and the bone 110 by providing an enhanced surface between the screw and the device, and an enhanced surface between device and the bone. The shim device 400 is adapted to allow for insertion of the pedicle screw 140 while leaving the base 141 of the screw accessible for attachment of the cross members 200 and other components (e.g., spacers 201) of the intervertebral stabilization system. Alternatively, in embodiments other than in spinal fusion surgeries, it is also possible that the shim device of present embodiments may be a component of other skeletal fixation systems when used to secure a bone screw in a patient.

In accordance with the foregoing description and Figures, lateral positioning of a shim device 400, 400' as described herein helps strengthen the engagement of a pedicle screw 140 to cortical bone 113 of the pedicle area 110 (and entering into the vertebral body 105)—especially at side locations of the pedicles where the pedicles are narrower—as the pedicle screw and shim device pass along the axis 114 (see axis 114 as shown in FIG. 3B) of the pedicle, and the device is also helpful in rescuing an incorrectly formed tract 703 through the pedicle.

In the preceding description, numerous details were set forth. It will be apparent, however, to one skilled in the art, that the present invention may be practiced without some of these specific details. Additionally, one of ordinary skill in the art will recognize the inventive principles disclosed are not limited to the embodiments disclosed herein, and that various aspects of the disclosed embodiments can be combined to achieve yet additional embodiments. In some instances, well-known structures and devices are shown in block diagram form, rather than in detail, in order to avoid obscuring the present invention.

While a preferred embodiment of the present disclosure has been shown and described, it will be apparent to those skilled in the art that many changes and modifications may be made without departing from the claimed subject matter in its broader aspects. For example, it will be appreciated that one of ordinary skill in the art may mix and match the various components of the various embodiments of the claimed subject matter without departing from the true spirit of the claims. The appended claims are therefore intended to cover all such changes and modifications as fall within the true spirit and scope of the invention.

What is claimed is:

1. A spinal bone shim attachment device adapted for use unilaterally with and engaging a pedicle screw to help avoid breaking out of the screw in a spinal bone during installation and use of the shim attachment device and screw, comprising:

an elongated partial shaft portion, having a base end and a tip end, said partial shaft portion being greater than 90 degrees but less than 270 degrees around when viewed in cross section;

a base portion connected with the base end of said partial shaft portion, the base portion being greater than 90 degrees but less than 270 degrees around when viewed in cross section;

a longitudinally extending concave surface within said partial shaft portion adapted for engaging the pedicle screw during use;

an asymmetric tip positioned opposite said base portion, and connected with the tip end of said partial shaft portion, said asymmetric tip comprising a point at a leading end of said asymmetric tip, at least one inner surface extending rearwardly and positioned inwardly from said point, a base surface at the tip end of said partial shaft portion and substantially normal to and intersecting with said at least one inner surface of said asymmetric tip, and at least one outer surface opposite said at least one inner surface and which connects with said partial shaft portion at the tip end of said partial shaft portion and at outer longitudinally-extending edges of said at least one inner surface ending at said point, said asymmetric tip and said partial shaft portion adapted for facilitating accurate placement of the shim to avoid or reconstruct a breach of cortical bone margins or to reconstruct breached cortical bone margins after a failed attempt; and a plurality of bone engaging ridges extending outwardly from and along at least a portion of the length of said shaft portion, said bone engaging ridges adapted for engaging bone and tissue, wherein said partial shaft portion, said base portion, and said tip, serve to guide the shim attachment device, and a subsequently installed screw, into a proper location while helping avoid the screw from breaking out of the spinal bone.

2. The spinal bone shim attachment device of claim 1, wherein at least one of said plurality of bone engaging ridges is comprised of a first edge positioned normal to said partial shaft portion and extends outwardly from said partial shaft portion, and a second edge that is oriented at an angle relative to said partial shaft portion and connects the first edge to said partial shaft portion.

3. The spinal bone shim attachment device of claim 2, wherein the first edge comprises a flat bottom edge, and wherein the second edge comprises a curve defined by an arc.

4. The spinal bone shim attachment device of claim 3, wherein the second curved edge and the first flat bottom edge intersect at a 90-degree angle.

5. The spinal bone shim attachment device of claim 1, wherein said tip further comprises a bias element for guiding proper placement of the shim attachment device and the screw into the spinal bone.

6. The spinal bone shim attachment device of claim 5, wherein the bias element comprises an angled outer surface of said tip surface relative to said elongated partial shaft portion and adapted for enhanced guiding of the spinal bone shim attachment device and the screw to proper placement during installation.

7. The spinal bone shim attachment device of claim 1, wherein the spinal bone shim attachment device is composed of polyether- ether-ketone (PEEK).

8. The spinal bone shim attachment device of claim 1, wherein said partial shaft portion is rounded as viewed in axial cross section.

9. The spinal bone shim attachment device of claim 1, wherein said tip comprises at least one tip edge, and wherein said partial shaft portion further comprises at least one partial shaft edge continuing from the at least one tip edge of said tip, the tip edge and the partial shaft edge adapted for enhanced guiding and slicing as said tip and said partial shaft portion are inserted.

10. The spinal bone shim attachment device of claim 1 wherein said plurality of bone engaging ridges are equidistant from one another.

11. The spinal bone shim attachment device of claim 10 wherein there are between 20 and 40 bone engaging ridges.

12. The spinal bone shim attachment device of claim 1, wherein the concave surface within said partial shaft portion further comprises a plurality of guide channels adapted for engaging the pedicle screw.

13. A spinal bone shim attachment device adapted for use unilaterally with and engaging a pedicle screw to help avoid breaking out of the pedicle screw in a spinal bone during installation and use of the shim attachment device and screw, comprising:

an elongated partial shaft portion, having a base end and a tip end, said partial shaft portion being greater than 90 degrees but less than 270 degrees around when viewed in cross section;

a base portion connected with the base end of said partial shaft portion, the base portion being greater than 90 degrees but less than 270 degrees around when viewed in cross section;

a longitudinally extending concave surface within said partial shaft portion adapted for engaging the pedicle screw during use;

an asymmetric tip positioned opposite said base portion, having a tip surface and connected with the tip end of said partial shaft portion and which is partially pyramid-shape and further comprises:

a point at a leading end of said tip;

a plurality of symmetrical slanted and longitudinally intersecting flat surfaces extending rearwardly and positioned inwardly from said point and toward a longitudinal axis of said tip;

a base surface at the tip end of said partial shaft portion and substantially normal to said plurality of intersecting flat surfaces of said tip; and an outer curved surface opposite said plurality of symmetrical slanted flat surfaces and which connects at outer longitudinally-extending edges of said plurality of slanted flat surfaces ending at said point;

a plurality of bone engaging ridges extending outwardly from and along at least a portion of the length of said shaft portion, said bone engaging ridges adapted for engaging bone and tissue as the shim is pushed through the pedicle into the vertebral body;

wherein said partial shaft portion, said base portion, and said tip serve to guide the shim attachment device and a subsequently installed pedicle screw, into a proper location while helping avoid the pedicle screw from breaking out of the spinal bone;

wherein said tip further comprises a bias element for guiding proper placement of the shim attachment device and the screw into the spinal bone; and wherein the bias element comprises an angled outer surface of said tip surface relative to said elongated partial shaft portion and adapted for guiding of the spinal bone shim attachment device and the screw to proper placement during installation.

14. The spinal bone shim attachment device of claim 13, wherein said base surface of said tip is positioned substantially normal to the longitudinal axis of said tip and intersects with said plurality of symmetrical slanted flat surfaces, said base surface being adapted for engaging a tip of the pedicle screw.

15. A spinal bone shim attachment device adapted for use unilaterally with and engaging a pedicle screw to help avoid breaking out of the pedicle screw in a spinal bone during installation and use of the shim attachment device and screw, comprising:
- an elongated partial shaft portion, having a length, having a base end and a tip end, said partial shaft portion being greater than 90 degrees but less than 270 degrees around when viewed in cross section;
- a base portion connected with the base end of said partial shaft portion, the base portion being greater than 90 degrees but less than 270 degrees around when viewed in cross section;
- a longitudinally extending concave surface within said partial shaft portion adapted for engaging the pedicle screw during use, said concave surface further comprising a plurality of guide channels adapted for engaging the pedicle screw wherein each of said plurality of guide channels further comprises a longitudinally-extending ridge which runs parallel to said partial shaft portion along the length of said partial shaft portion;
- an asymmetric tip positioned opposite said base portion, and connected with the tip end of said partial shaft portion;
- a plurality of bone engaging ridges extending outwardly from and along at least a portion of the length of said shaft portion;
- wherein said partial shaft portion, said base portion, and said tip, serve to guide the shim attachment device and a subsequently installed pedicle screw, into a proper location while helping avoid the pedicle screw from breaking out of the spinal bone.

16. The spinal bone shim attachment device of claim 15, wherein there are 4 guide channels defined by 3 longitudinally extending ridges.

17. An improved method for placement of a pedicle screw in a vertebral body comprising:
  providing a pedicle screw;
  providing a spinal bone shim attachment device for coupling to a pedicle screw, the shim attachment device comprising:
    an elongated unilaterally-disposed partial shaft portion greater than 90 degrees but less than 270 degrees around when viewed in cross section, having a length and having an outer surface;
    a unilaterally-disposed base portion greater than 90 degrees but less than 270 degrees around when viewed in cross section;
    a concave inner surface within said partial shaft portion adapted for engaging the pedicle screw;
    an asymmetric edged tip on the partial shaft portion and positioned opposite said base portion; and
    a plurality of bone engaging ridges extending away from said shaft portion and positioned along said length of said shaft portion;
  making an incision with a piercing member creating a pilot track extending from the skin surface of a patient through the pedicle and into the vertebral body;
  preparing the incision to access the pedicle for the insertion of the spinal bone shim attachment device by opening the skin and, by using known dissection techniques, making a pilot hole in the pedicle by using a biased pedicle probe in order to create a track down to the vertebral body;
  inserting the spinal bone shim attachment device through the pedicle into the vertebral body with the outer surface of the device facing away from the spinal cord, and with the concave inner surface of the device facing towards the spinal cord; and
  inserting the pedicle screw into the pilot track adjacent and between the spinal bone shim attachment device and the spinal cord.

18. An improved method for improving patient outcomes in spinal fusion surgery where an improperly-angled incision has been made on the patient comprising:
  providing a pedicle screw;
  providing a spinal bone shim attachment device adapted for guiding and engaging the pedicle screw, the device comprising:
    an elongated unilaterally-disposed partial shaft portion greater than 90 degrees but less than 270 degrees around when viewed in cross section and having an outer surface and a length;
    a unilaterally-disposed base portion greater than 90 degrees but less than 270 degrees around when viewed in cross section;
    a concave inner surface within said partial shaft portion adapted for engaging the pedicle screw;
    an asymmetric edged tip on the partial shaft portion and positioned opposite said base portion; and
    a plurality of bone engaging ridges extending outwardly from said shaft portion and positioned along a length of said partial shaft portion;
  making a proper incision at a correct angle with a piercing member by opening the skin and, by using known dissection techniques, making a pilot hole in the pedicle by using a biased pedicle probe in order to create a track down to the pedicle and so creating a pilot track relative to a previously-made improper-angle incision extending from the skin surface of the patient through the pedicle into the vertebral body;
  inserting the spinal bone shim attachment device through the proper incision, through the pedicle, and into the vertebral body with the outer surface of the device facing away from the spinal cord, and with the concave inner surface of the device facing towards the spinal cord, with the spinal bone shim attachment device covering an entryway into the improper incision; and
  inserting the pedicle screw into the pilot track adjacent and between the spinal bone shim attachment device and the spinal cord.

* * * * *